United States Patent [19]

Fong et al.

[11] Patent Number: 4,863,016
[45] Date of Patent: Sep. 5, 1989

[54] PACKAGING FOR A STERILIZABLE CALIBRATABLE MEDICAL DEVICE

[75] Inventors: Conrad T. O. Fong, Redmond, Wash.; Richard W. Grabenkort, Bearrington, Ill.; Scott P. Huntley, Concord, Calif.

[73] Assignee: Abbott Laboratories, Abbott Park, Ill.

[21] Appl. No.: 224,425

[22] Filed: Jul. 25, 1988

[51] Int. Cl.$^4$ ................................................ B65D 79/00
[52] U.S. Cl. ...................................... 206/210; 206/439
[58] Field of Search ............... 206/210, 438, 439, 370, 206/363

[56] References Cited

U.S. PATENT DOCUMENTS

| | | |
|---|---|---|
| 3,728,839 | 4/1973 | Glick .............................. 206/210 X |
| 3,967,728 | 7/1976 | Gordon et al. . |
| 4,312,171 | 1/1982 | Vadas . |
| 4,366,901 | 1/1983 | Short ................................... 206/210 |
| 4,522,302 | 6/1985 | Paikoff . |
| 4,538,395 | 9/1985 | Edmonds et al. . |
| 4,620,633 | 11/1986 | Lookholder . |
| 4,632,244 | 12/1986 | Landau . |
| 4,732,850 | 3/1988 | Brown et al. . |

Primary Examiner—William Price
Attorney, Agent, or Firm—Christensen, O'Connor, Johnson & Kindness

[57] ABSTRACT

The present invention provides a package for and method of packaging a sterilizable calibratable medical device including a hydratable sensor component. The device is maintained in a sterile environment during storage and in a clean environment during the calibration procedure. The package includes a manifold connected to the sensor component by plumbing. The plumbing establishes fluid communication between the manifold and the sensor component and/or between the sensor component and the ambient environment of the plumbing. The manifold, plumbing and medical device are sealed in a wrap including a gas-permeable surface. The wrap and its contents, including the interior surfaces of the components, are sterilizable by exposing the wrap to a gaseous sterilization solution and appropriately adjusting the plumbing. The medical device is hydratable by directing the hydration solution to the sensor component by means of the plumbing. In order to store the package over an extended period of time, a gas-impermeable chamber is defined which includes the ambient environment of the plumbing. The gaseous environment of the medical device is thereby controllable. In this manner, the device is prepared for calibration and is storable in the sterile environment. By connecting a reservoir including calibration solution to the plumbing, the calibration solution is directed to the sensor component without removing the medical device from its clean enviroment. The temperatures of the sensor component and the solution are controlled throughout the calibration process in order to ensure that the device is calibrated in accordance with its intended use. The present invention further discloses a solution for preparing the medical device for use. The solution is chemically compatible with the intended use of the device.

9 Claims, 4 Drawing Sheets

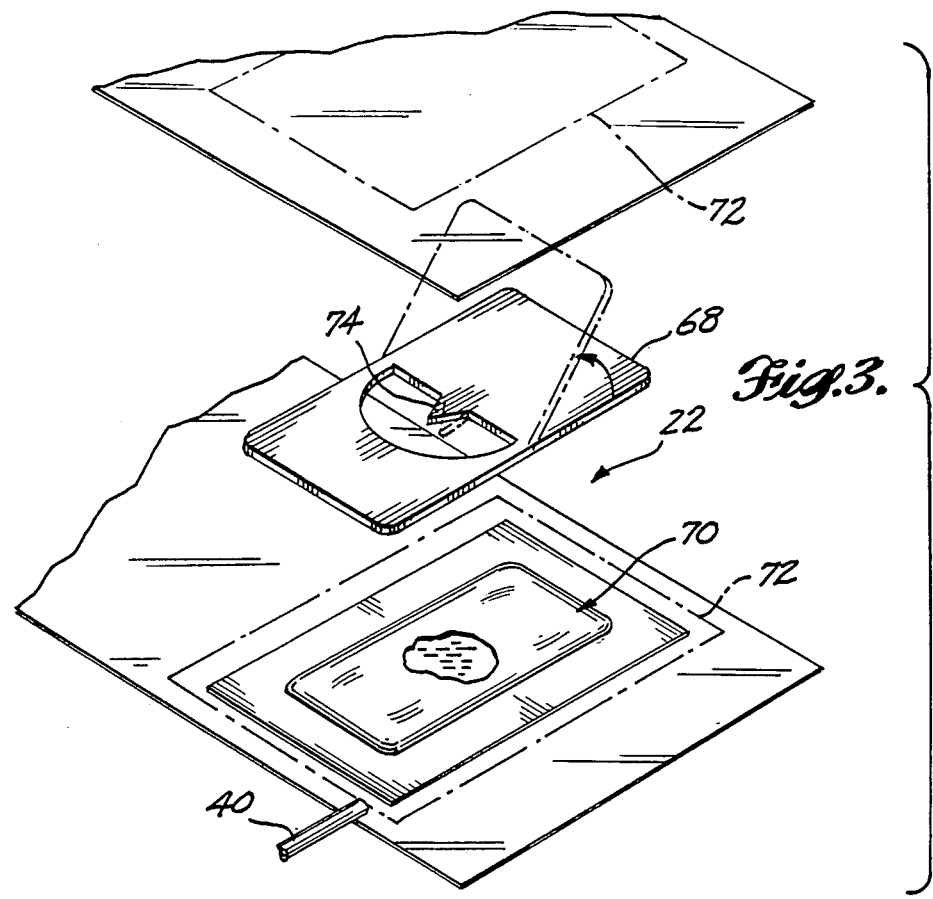
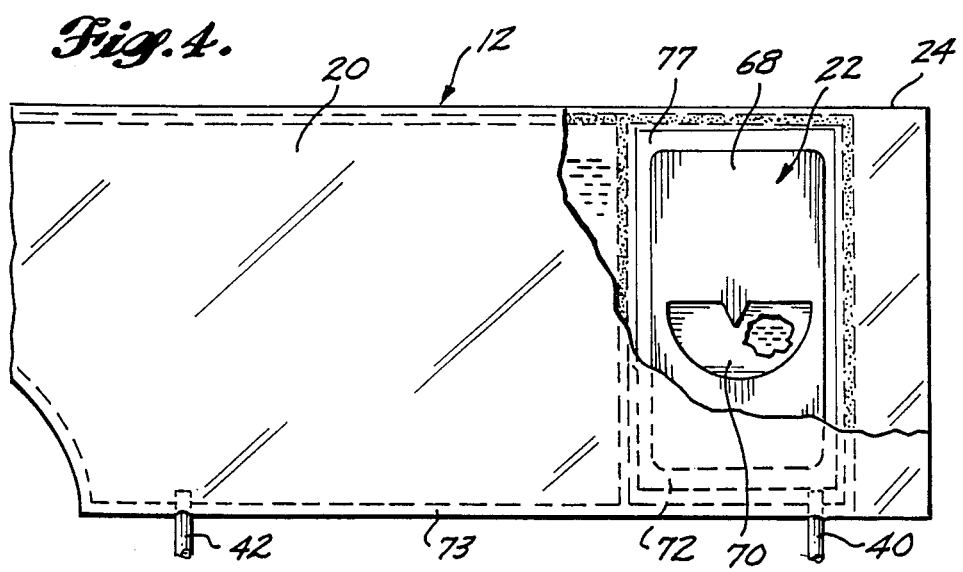

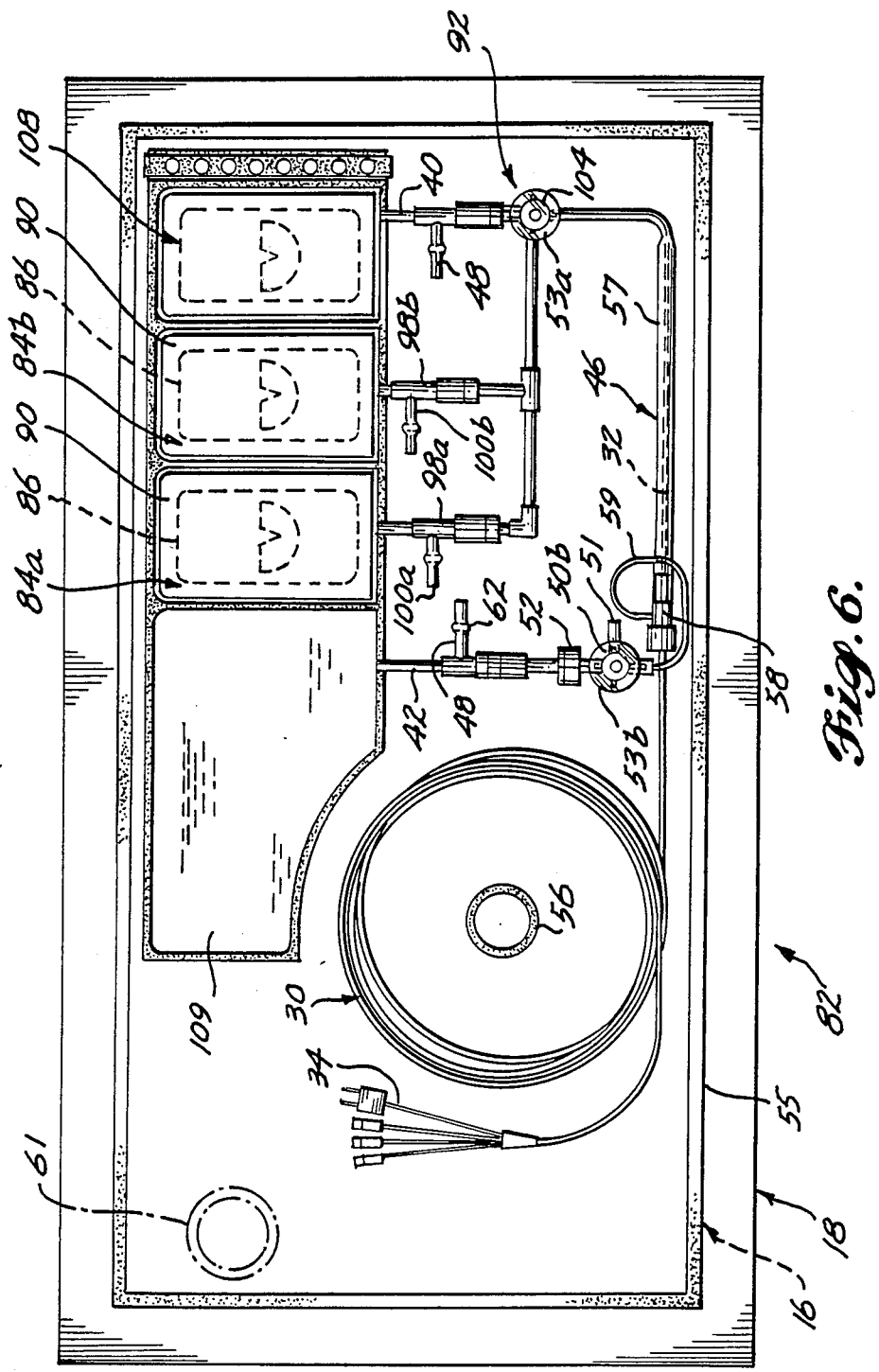

PACKAGING FOR A STERILIZABLE CALIBRATABLE MEDICAL DEVICE

TECHNICAL FIELD

This invention relates to packages for and methods of packaging sterilizable calibratable medical devices and, more particularly, provides a packaging system for in situ sterilization and calibration of medical devices consisting of hydratable sensor components.

BACKGROUND OF THE INVENTION

Packages for and methods of packaging medical devices are numerous. The choice of method for packaging a device depends in part on the intended use of the device. Factors include whether the device is used in a sterile environment, whether the device is used in contact with or inserted into a living animal, whether the device is disposable, etc. Certain devices must be sterilized prior to use. One known method for packaging a sterile device is to first insert the device into a gas-impermeable wrap. The interior of the wrap, including the device, is then sterilized. The wrap is then sealed so that the device remains sterilized until the package is opened just prior to use. Once the package is opened, a minimum amount of handling is desirable to avoid the possibility of contaminating the device.

Certain medical devices additionally require calibration prior to use. Medical devices that monitor analyte levels, temperature, etc., often include chemical or electrical sensing components that are very sensitive to temperature, moisture, etc. These devices are generally used in conjunction with monitoring instrumentation that controls and records the monitoring process. For example, a medical device may be connected to a computerized controller which initiates and transmits an electrical or optical signal to the device, receives a resultant signal from the device, and analyzes the resultant signal to produce a value indicative of the measured characteristic.

One common way of calibrating a medical device used for monitoring analyte concentrations is to immerse the sensing component of the device into a calibration solution containing a known amount of the targeted analyte. Base measurement levels are recorded in accordance with the known amount of the analyte. Such calibration solutions must be highly uniform to provide consistent and useful results in the calibration process. The solutions are typically unstable and are only prepared as needed or prepackaged in glass ampules. Glass ampules require especially careful handling during the calibration process to avoid breakage. Shelflife problems, e.g., change of chemistry, separation, etc., may be encountered with prepackaged solutions that are stored over a period of time prior to use. Conventional calibration procedures are time-consuming, costly, subject the device to possible contamination, and often require the presence of a trained technician to oversee the process. Additionally, if a calibratable device is to be stored over a period of time, the device is most easily stored in a dry state to avoid problems arising from the storage of a moist device. Bringing the sensing component of the device from a dry to a functional state often requires hydrating the sensing component over an extended period of time.

When a device must be sterilized as well as calibrated, additional problems arise due to the fact that the sterilization and calibration procedures are often incompatible. For example, one common method of sterilizing a medical device is to expose the device to ethylene oxide (ETO). The ETO procedure is carried out in a non-liquid, i.e., dry, environment. This dry state renders the sensing component of the device completely nonfunctional if the component is meant to operate in a moist environment. In contrast, as discussed above, the common method of calibrating such a device is to immerse the device in a calibration solution. Thus, an ETO sterilization procedure and a moist calibration procedure must be distinct phases in the preparation of the device.

In recent years, optical fiber sensors, also known as optrodes, have been developed to detect the presence of and to continuously monitor the concentration of various analytes, including oxygen, carbon dioxide, glucose, inorganic ions, and hydrogen ions, in solutions. An example of such a sensor is a blood gas sensor for monitoring pH, $PCO_2$, or $PO_2$. Such a blood gas sensor is based on the recognized phenomenon that the absorbance or luminescence of certain indicator molecules is specifically perturbed in the presence of certain analytes. The perturbation in the absorbance and/or luminescence profile is detected by monitoring radiation that is reflected or emitted by the indicator molecule when it is in the presence of a specific analyte. The targeted analyte is generally a part of a solution containing a variety of analytes.

Optrodes have been developed that position an analyte-sensitive indicator molecule in the light path at the end of one or more optical fibers. This fiber unit is often termed the sensor component. The sensor component is an integral part of a blood gas catheter. The indicator molecule is typically housed in a sealed chamber at the end of the fiber(s). The chamber is secured to the optical fiber by a suitable cement material. The walls of the chamber are permeable to the analyte. The sensor component is inserted into and left in a patient for an extended period of time. Analyte readings in the form of optical signals are transmitted from the sensor component to monitoring instrumentation which analyzes the signals and controls the monitoring process.

The sensor component in a blood gas catheter thus typically includes a membrane material, an analyte sensing material, an optical fiber, and a cement. Each element is chosen to be compatible with the other elements and with the monitoring process. In order to monitor a specific analyte, the sensor component is sterilized and then brought to a functional state in which the catheter sensor is responsive to the targeted analyte. Additionally, the monitoring instrumentation is calibrated in conjunction with the specific catheter prior to use. If the catheter is subject to the above-described ETO sterilization and packaging process, the analyte sensing material of the sensor is completely dried and is not in proper chemical balance to carry out the monitoring process. Thus, the sensor must be hydrated and calibrated prior to use. If the traditional calibration method described above is carried out, the catheter is exposed and may be contaminated.

The package and method of packaging of the present invention overcomes these and other problems in the prior art.

SUMMARY OF THE INVENTION

The present invention provides a package for a sterilizable calibratable medical device such that the device is maintained in a clean environment during the calibration procedure. The medical device includes a hydratable sensing component. The package includes a wrap enveloping the medical device, first and second reservoirs, and a plumbing device. The wrap includes a gas-permeable surface. The first reservoir is substantially filled with a hydration solution which is suitable for hydrating the sensor component. The second reservoir is substantially evacuated and is sized to hold all of the liquid solution to be used in the preparation of the device. The plumbing device is adapted to reversibly establish, without breaching the wrap, either gaseous communication between the gas-permeable surface and the sensor component, or liquid communication between the first reservoir, the sensor component, and the second reservoir. In order to sterilize the device, plumbing, and the reservoirs, the plumbing device is adapted to establish gaseous communication between the sensor component and the ambient environment of the plumbing device, and the package is exposed to sterilizing gas. The gas passes through the gas-permeable surface and the plumbing device to the sensor component.

In accordance with other aspects of the present invention, a gas-impermeable chamber is defined which includes the ambient environment of the plumbing device. In this manner, the gaseous composition of the ambient environment of the plumbing device is controlled. The chamber may be defined by a bag suitable for enveloping the wrap.

In accordance with further aspects of the present invention, the package includes a delivery device for delivering the hydration solution from the first reservoir into the plumbing device. Accordingly, the first reservoir is rupturable by the delivery means. The first reservoir is ruptured and the hydration solution is directed to the sensor component in order to hydrate the sensor component.

In accordance with additional aspects of the present invention, the sensor component includes at least one optical fiber.

In accordance with still further aspects of the present invention, the plumbing device is adapted to reversibly establish liquid communication between the ambient environment of the package, the sensor component, and the second reservoir. In this manner, calibration solution that is held in a container exterior to the wrap is directed to the sensor component without removing the medical device from its clean environment, thereby reducing the possibility of contamination.

In accordance with still further aspects of the present invention, the package includes a third reservoir substantially filled with a calibration solution suitable for calibrating the sensor. The plumbing device is adapted to reversibly establish, without breaching the wrap, liquid communication between the third reservoir, the sensor component, and the second reservoir. The device is attached to monitoring instrumentation by removing the device cables from the wrap at a point remote from the sensor component and connecting them to the instrumentation. In this manner, the device is calibrated without removing the medical device from its clean environment. Additionally, the temperatures of the calibration solution and the sensing component are controlled throughout the calibration process to ensure that the calibration measurements are obtained at a temperature substantially equivalent to the temperature at the point of use.

The packaging technique of the present invention allows a blood gas catheter to be calibrated immediately prior to use without the need for a blood gas analyzer to obtain a reference value if the blood gas analyzer values for the calibration solution are well known. The calibration technique is practical and allows calibration using aseptic handling that protects the cleanliness of the medical device and minimizes the possibility of contamination of the sensor component.

BRIEF DESCRIPTION OF THE DRAWINGS

FIG. 3 is an exploded isometric view of a solution reservoir in accordance with the present invention;

FIG. 4 is a top perspective view of a manifold in accordance with the present invention;

DETAILED DESCRIPTION OF THE PREFERRED EMBODIMENTS

Figure 1:
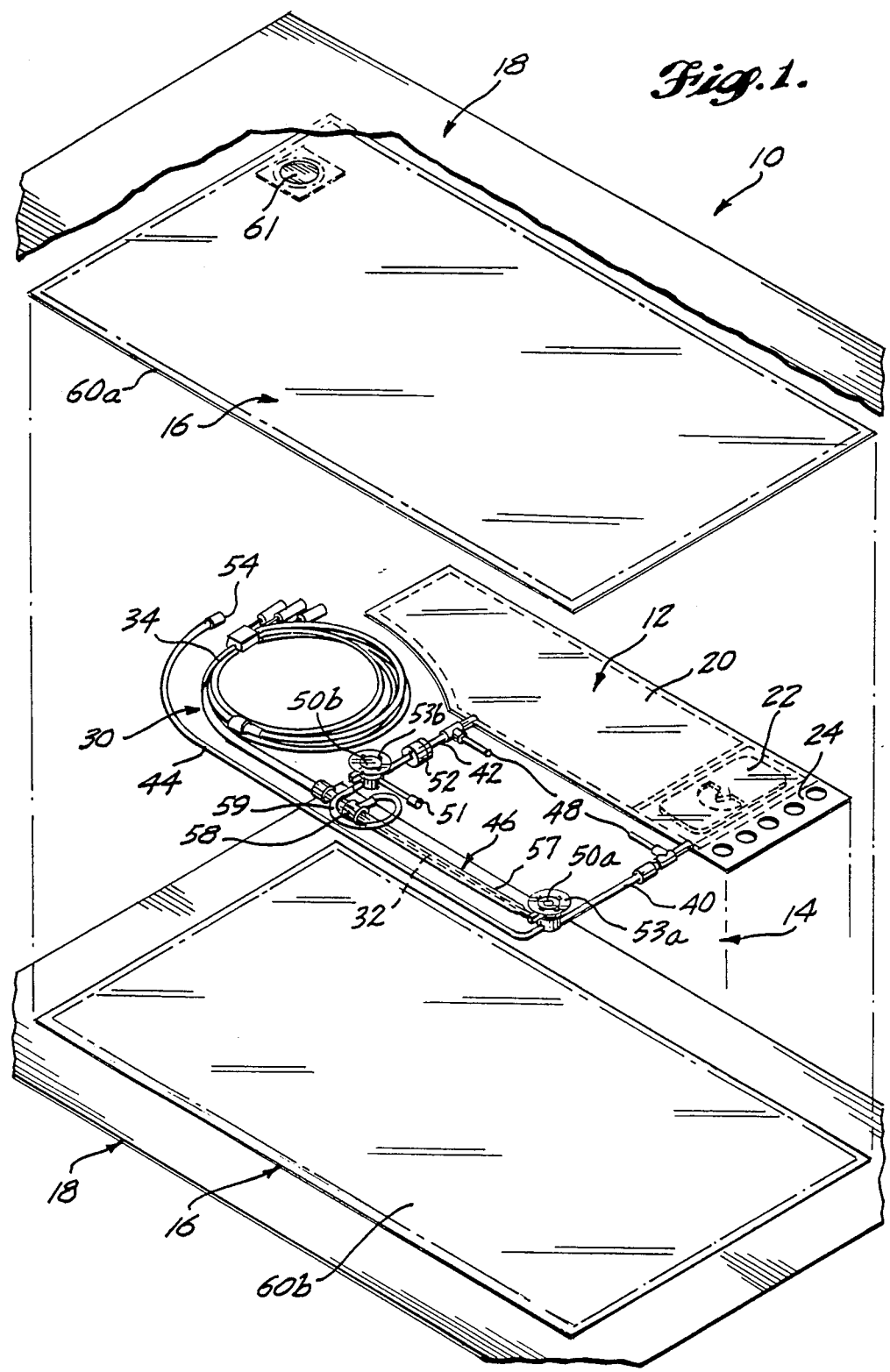
FIG. 1 is an exploded isometric view of a package in accordance with the present invention.

With reference to FIG. 1, one preferred embodiment of package 10 includes manifold 12, plumbing 14, inner wrap 16, and outer wrap 18. The manifold includes deposit reservoir 20, hydration reservoir 22, and flap 24. The deposit reservoir 20 and hydration reservoir 22 are connected to a medical device such as catheter 30 by plumbing 14. The plumbing is connected to the catheter at the sensor component 32 which includes the analyte sensing components of the catheter. The sensor component may also include a temperature measuring component. The sensor component 32 is disposed within the plumbing. The catheter also includes one or more instrumentation cables 34 which ultimately connect the catheter 30 to the remainder of the medical monitoring device (not shown). The sensor component extends from the cable 34. At the sensor-cable connecting point, a cable flange (not shown) extends radially from the cable.

The plumbing 14 includes hydration tube 40, flush tube 42, calibration tube 44, delivery device 46, sterilization tubes 48, stopcocks 50a and 50b, gas filter 51, and directional valve 52. Preferably, all of the tubing in plumbing 14 is polyvinyl chloride (PVC) tubing. Such tubing is easy to handle and is slightly gas-permeable over an extended period of time.

The stopcocks 50 are three-way adjustable valves. The settings of the stopcocks are manually adjustable and are easily manipulated through the packaging materials. The stopcocks are used to control the flow of solution through the plumbing. Caps 53a and 53b overlay the stopcocks in order to protect the packaging material from damage caused by protrusions on the stopcocks.

Hydration tube 40 is in full communication with hydration reservoir 22, a sterilization tube 48, and stopcock 50a. Flush tube 42 is in full communication with the deposit reservoir 20, a sterilization tube 48, and directional valve 52. Directional valve 52 allows solution to flow through flush tube 42 into the deposit reservoir and prevents solution flow in the opposite direction. Calibration tube 44 is in full communication with filter 54 and stopcock 50a. Filter 54 is preferably a hydrophobic filter through which gaseous solutions freely pass and which prevents the passage of liquid solutions.

Delivery device 46 includes catheter tube 57, joint 58 and connect tube 59. One end of catheter tube 57 is connected to stopcock 50a. The other end of the catheter tube is connected to joint 58. Joint 58 connects catheter tube 57, connect tube 59 and cable 34. The connect tube is connected to stopcock 50b. The joint provides fluid communication between the catheter tube and the connect tube. Delivery device 46 is preferably used to deliver the sensor component to the patient, i.e., the delivery device is an integral component of the blood gas catheter. Thus, the materials used for delivery device 46 are compatible with the packaging procedure as well as with the blood gas monitoring procedure.

The sensor component extends from cable 34, through joint 58 and into catheter tube 57. The joint includes a ring seal (not shown) through which the sensor component extends and against which the cable flange is pressed. The ring seal and flange prevent the flow of solution from the joint to the cable. The position of the cable and sensor component relative to the joint is fixed by a suitable attachment mechanism such as a nut screwed over the joint and against the flange. In this manner, any fluid flowing between stopcock 50a and 50b passes over the sensor component.

Stopcock 50b is connected to filter 51 and directional valve 52. Filter 51 is preferably a hydrophobic filter through which gaseous solutions freely pass and which prevents the passage of liquid solutions.

The plumbing establishes gaseous communication between the sensing component and the plumbing ambient environment by means of sterilization tubes 48, filter 51, and filter 54. The plumbing also establishes liquid communication between the manifold reservoirs and the sensor component by hydration tube 40, delivery device 46, and flush tube 42.

Inner wrap 16 includes sides 60a and 60b. Side 60a includes filter 61 along one edge. The filter 61 is preferably a bacterial retentive hydrophobic filter. An exemplary filter 61 is a fibrous paper-like membrane manufactured by E. I. DuPont de Nemours & Co. and referred to by the trademark TYVEK. The filter allows gas exchange between the interior and exterior of inner wrap 16 when the wrap is otherwise sealed in a gas-impermeable manner. The remainder of the material of side 60a is preferably clear so that the packaging is easily viewable therethrough. The material is also relatively thin and flexible so that the adjustments to the packaging, e.g., the stopcocks, are easily carried out through the wrap.

Figure 2:
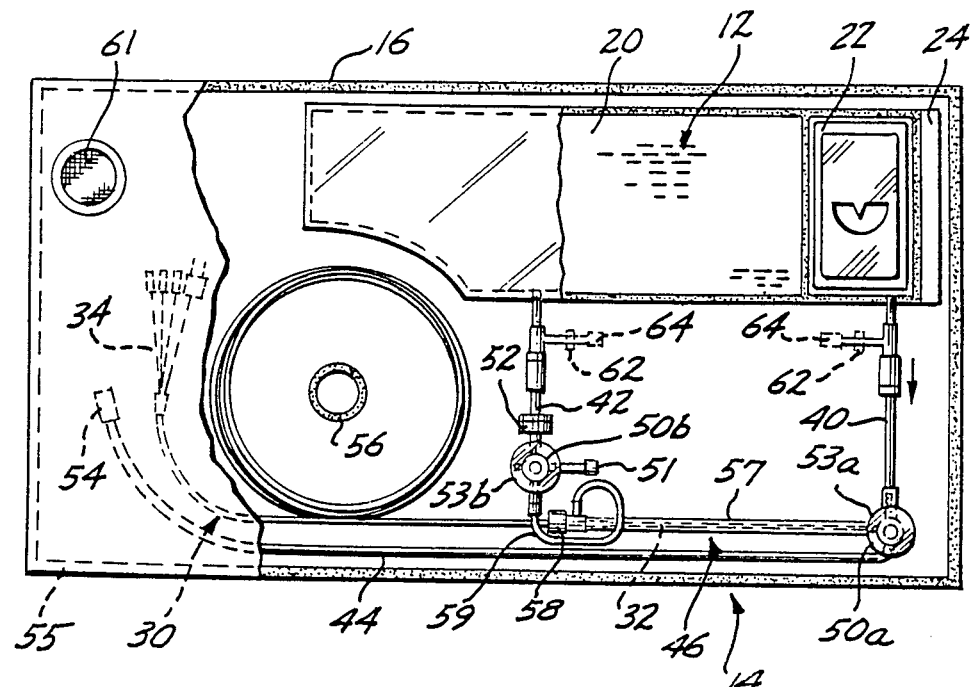
FIG. 2 is a top perspective view of a package in accordance with the present invention.

During the packaging process, catheter 30 is sterilized dry, and then hydrated and prepared for calibration. With reference to FIG. 2, hydration reservoir 22 and deposit reservoir 20 are connected to catheter 30 at sensor component 32 by plumbing 14. These components are placed between the sides 60a and 60b of inner wrap 16 and the outside edges of the inner wrap are completely sealed by edge seals 55. Flap 24 of the manifold is caught between the edge seals to secure the position of manifold 12 within inner wrap 16. Additionally, seal 56 preferably secures the position of catheter 30 within the inner wrap by securing the gathered cable 34. The manifold 12 and catheter 30 are positioned within the inner wrap so that plumbing 14 is and remains untangled relative to the catheter, and so that access to filter 61 is not blocked. Once the inner wrap edges are sealed, filter 61 is the only means of gaseous communication between the interior and the exterior of the wrap.

Prior to the sterilization process, stopcocks 50 are open so that the lumens of the hydration tube, calibration tube, catheter tube, connect tube, and flush tube are all in fluid communication. In order to sterilize the catheter, sealed inner wrap 16 functions as a breather bag. The wrap is simply a gas-permeable container which acts to keep the gaseous environment within it free from bacteria and germs. A sterilizing gaseous solution, preferably ethylene oxide (ETO), is pumped into inner wrap 16 through filter 61. This is performed by pressurizing the atmosphere surrounding inner wrap 16. The ETO flows freely over catheter 30, plumbing 14 and manifold 12. Additionally, the ETO flows into plumbing 14 through sterilization tubes 48, filter 51, and filter 54. In this manner, sensor component 32 and the interior surfaces of the plumbing and the manifold are sterilized. After sterilization, the ETO is outgassed from inner wrap 16 by allowing the inner wrap to stand and the ETO to dissipate in a controlled environment.

Preferably, all surfaces and passageways of manifold 12, plumbing 14, and catheter 30 are sterilized during the ETO procedure. Certain joints and attachments in plumbing 14 may be so tight that they are essentially ETO impermeable and therefore hinder or restrict access of ETO. These joints and attachments are loosened prior to the sterilization procedure and are tightened immediately thereafter.

After sterilization, sterilization tubes 48 are sealed with seals 62 (shown in reference). Preferably, tubes 48 are sealed by a radio frequency (RF) sealing technique. This technique affects a heat seal without affecting the integrity of inner wrap 16. After seals 62 are in place, the only points of entry remaining in plumbing 14 are through manifold 12 via hydration tube 40 and flush tube 42, filter 51, or through filter 54. Alternatively, sterilization tubes 48 include filters 64 (shown in reference). Filters 64 are preferably hydrophobic filters which allow gaseous solutions to pass freely through, but liquid solutions, such as the hydration solution, are not allowed to pass through. If such filters are used, the sterilization tubes 48 do not require sealing after the sterilization process.

During the foregoing ETO sterilization procedure, the surfaces exposed to the ETO are completely dried. Thus, sensor component 32 is rendered nonfunctional since it operates in a moist environment. Sensor component 32 must be hydrated after sterilization and prior to use. Manifold 12 and plumbing 14 are used to hydrate the sensor component without removing it from its sterile environment within inner wrap 16.

In order to hydrate sensor component 32 within the sterile environment of inner wrap 16, a hydration solution is included within the inner wrap. The hydration solution is held and protected throughout the sterilization procedure in hydration reservoir 22. After sterilization, the hydration solution is released from hydration reservoir 22. Manifold 12, in conjunction with plumbing 14, delivers the hydration solution to sensor component 32 which is the portion of catheter 30 which requires hydration to be functional. The remainder of the catheter is maintained in a dry state.

With reference to FIG. 3, one preferred hydration reservoir 22 includes rupture plate 68, container 70, and outer envelope 72. Container 70 is suitable for holding a liquid such as a hydration solution or calibration solution. Container 70 protects the solution from contact with the ETO which is highly toxic. The container material is impermeable to ETO and is capable of withstanding the pressure and temperature changes that occur during a standard ETO sterilization process. In this manner, the solution is maintained in a sterile and nonpyrogenic state. Additionally, the container material is rupturable by mechanical pressure as will be discussed below. One suitable material for container 70 is foil-polypropylene laminated film.

Rupture plate 68 is preferably made up of a relatively rigid material. The plate is flat and corresponds in surface area to the surface of container 70. The rupture plate includes point 74 which, under adequate mechanical pressure, turns downwardly towards container 70 to rupture the container. The rupturing position is shown in reference.

With reference to FIG. 4, outer envelope 72 is formed about container 70 and rupture plate 68 so that there is adequate room within the envelope for the solution to flow from the container into the envelope and to hydration tube 40. Envelope 72 and deposit reservoir 20 are preferably made from two pieces of material that are connected by seals 73 (shown in reference) so that deposit reservoir 20, envelope 72, and flap 24 are formed. Container 70 is configured so that the container does not block the hydration tube when sealed within envelope 72. Flat edges 77 along the perimeter of container 77 aid in this positioning. Hydration tube 40 and flush tube 42 are sealed in communicating relationship with the interior of envelope 72 and the interior of deposit reservoir 20, respectively.

Referring again to FIG. 2, in order to hydrate sensor component 32, stopcock 50a is adjusted so that the fluid path betwen hydration tube 40 and catheter tube 57 is open. Stopcock 50b is adjusted so that the fluid path between connect tube 59 and valve 52 is open. Container 70 is ruptured as discussed above. The contents of the container are forced into envelope 72 by applying uniform pressure to rupture plate 68 against the container. The hydration solution flows through envelope 72 and hydration tube 40 to delivery device 46. Once the delivery device is filled with hydration solution, stopcocks 50a and 50b are adjusted in order to close off the delivery device thereby securing the solution over sensor component 32. The solution is held there in order to adequately hydrate the sensor component. Preferably, some of the hydration solution is held in the delivery device during the storage period, i.e., until calibration takes place. In this manner, sensor component 32 is held in a hydrated state during the storage period.

Preferably, the hydration fluid contains a chemical composition the same or very close to the composition contained in the initial calibration solution to be used with the device. Each solution content is highly sensor specific. The hydration solution may be formulated to also act as a calibration solution and be used to establish a first calibration point of the sensor component, e.g., by equilibrating the hydration-calibration solution with gases at levels appropriate for calibration of the specific analyte sensor in sensor component 32.

After sensor hydration has taken place, catheter 30 is preferably incubated to aid in returning the catheter to a functional state, and to stabilize the sensor component chemistry. Sensor component 32 is incubated in the hydration solution that is held within catheter tube 57.

To ensure the chemical balance of the solution is held constant, the package itself is incubated in a gas controlled environment. Inner wrap 16 is placed in a gas-impermeable container and flushed with a gaseous solution. The gaseous solution in which the inner wrapper and contents are incubated has chemical characteristics that are essentially the same as those of the dissolved gases in the hydration solution. The gaseous solution is also pre-equilibrated with water, i.e., the solution is hydrated. This characteristic of the gaseous solution prevents the solution from drawing the water off of the hydration solution held within delivery device 46. The gaseous solution passes through filter 61 into the interior of the inner wrap. Because of this controlled environment external to plumbing 14, no change in the chemical composition of the hydration solution will be affected due to the slight gas-permeability of delivery device 46. The dissolved gases in the hydration solution are thus maintained at the desired level. The time period, temperature, and gaseous composition for incubation are highly dependent on the sensor component elements and intended use.

For storage purposes, the gas-permeable portions of inner wrap 16 are sealed off. Preferably, the wrap is placed within outer wrap 18. The outer wrap is gas-impermeable and acts to seal the inner wrap gas-permeable sections including filter 61. Outer wrap 18 creates a constant gaseous environment surrounding catheter tube 57 and sensor component 32. A gaseous solution is pumped into the outer wrap and passes into inner wrap 16 through filter 61. The gaseous solution preferably has similar chemical characteristics to the incubation solution and the hydration solution. Again, the controlled environment ensures that the composition of gases dissolved in the hydration solution will not be altered by gaseous exchange through the delivery device. In this manner, the chemical composition of the hydration solution in the delivery device is maintained at a constant level throughout the storage period. Prior to use, depending upon the specific sensor component, it may be preferable to again incubate the entire package to further enhance the response of the sensor component.

Figure 5:
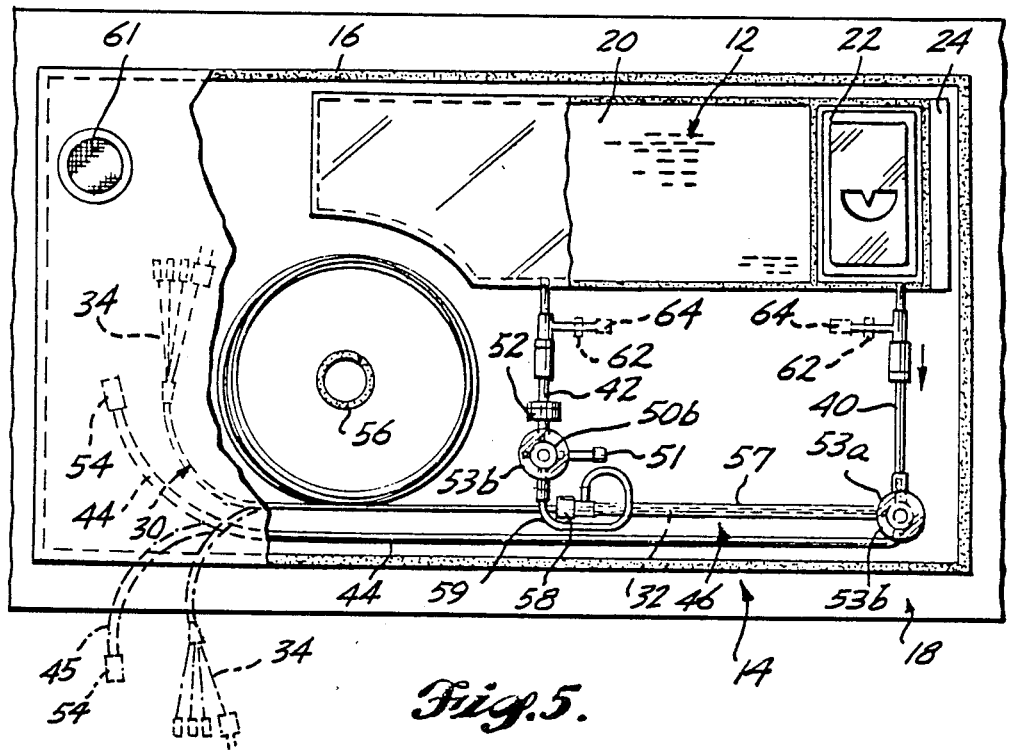
FIG. 5 is a top perspective view of a package in accordance with the present invention with the instrumentation cable of the medical device and the calibration tube of the package exposed in order to calibrate the medical device; and, FIG. 6 is a top perspective view of a medical device sealed in the inner wrap of a package including sterilizable calibration solution reservoirs in accordance with the present invention.

With reference to FIG. 5, calibration tube 44 and cable 34 are removed from both inner wrap 16 and outer wrap 18 at a point remote from the sensor component 32. The cables are connected to monitoring instrumentation (not shown). In this manner, the readings obtained by the catheter 30 are transmitted to the monitoring instrumentation.

Preferably, calibration tube 44 is small-bore tubing that has a small volume. This configuration reduces the amount of fluid that must be displaced when one or more calibration solutions are introduced into the plumbing.

To calibrate the device, two calibration solutions are typically used. Each solution contains a predetermined concentration of the targeted analyte. Filter 54 is removed from calibration tube 44 and an injection device (not shown) is attached thereto. A container of calibration solution is attached to the injection device. The injection device preferably includes a stopcock. The calibration solution passes from the container through calibration tube 44 and stopcock 50a to catheter tube 57 and connect tube 59. Stopcock 50b is set so that the solution flows through the stopcock to deposit reservoir 20 until enough solution from the delivery device 46 has been displaced to ensure that all of the solution held within the delivery device is the first calibration solution. At that point, the stopcock on the injection device is closed to hold the calibration solution within the delivery device.

Preferably, the temperatures of the calibration solution and sensor component are controlled throughout the calibration process. The temperatures are brought to and maintained at a temperature substantially equivalent to the temperature of the point of use of the sensor component, e.g., body temperature for a blood gas catheter. This control ensures that the calibration measurements taken are accurate. The temperature of the calibration solution is adjusted while the solution is in the container prior to delivery to the sensor component. The temperature of the wrap and its contents is adjusted by inserting the wrap between the sides of a thermal blanket. The wrap remains enveloped by the thermal blanket throughout the calibration procedure. In this manner, the sensor component is maintained in its clean environment during the calibration procedure. If the sensor component includes a temperature sensing component, the temperature sensing component is utilized to provide component temperature information.

Once the calibration solution is delivered to the delivery device and the temperature of the sensing component stabilized, analyte measurements are taken via cables 34. Once the measurements are taken, the injection device stopcock is opened and a second solution is transmitted to delivery device 46 in a similar manner. As an alternative method of retaining the hydration solution within the delivery device, stopcocks 50a and 50b are closed to hold the solution therebetween while the calibration measurements are taken.

Once calibration is completed, a parenteral grade saline solution is flushed through the plumbing to wash out any remaining calibration solution. The solution is introduced to the plumbing through calibration tube 44. The catheter is then removed from the package by disconnecting the delivery device from the remainder of the plumbing. The joints at stopcocks 50a and 50b are disconnected and delivery device 46 and sensor component 32 are removed as a unit. The remainder of the package is disposed of.

Since all solutions are flushed into deposit reservoir 20, the reservoir is sized so that its capacity is equal to or greater than the total volume of all of the hydration, calibration, and cleaning solutions to be used to prepare the catheter for use.

With reference to FIG. 6, a preferred package embodiment 82 is similar to package 10, but includes calibration reservoirs 84a and 84b, each containing a separate calibration solution, as well as reservoir 85 containing a hydration solution. (Similar components between packages 82 and 10 will be referred to with the same reference numbers.) The calibration reservoirs are similar to reservoir 22 of package 10. Each reservoir includes a rupture plate 86, a container (not shown), and an envelope 90. The plumbing 92 includes calibration tubes 98a and 98b, sterilization tubes 100a and 100b, and passage tube 102. The calibration tubes are connected to the calibration reservoirs along the seals of envelopes 90a and 90b. The calibration tubes are connected to passage tube 102 which is connected to stopcock 104. Stopcock 104 is similar to stopcock 50a. The remainder of plumbing 92 is similar to plumbing 14. The package also includes deposit reservoir 109 sized so as to receive all of the hydration and calibration solutions and any cleaning solutions to be used.

To prepare catheter 30 for use, an ETO sterilization procedure as described above is carried out. Sensor component 32 is then hydrated and incubated. Inner wrap 16 is packaged in outer wrap 18 for storage purposes. Prior to use, cables 34 are removed from the inner and outer wraps and connected to monitoring instrumentation. Calibration reservoir 84a, including the first calibration solution, is ruptured and the solution directed into delivery device 46. The stopcocks are adjusted to hold the solution in the delivery device. The temperature of the sensor component is controlled as described above. Calibration measurements are taken when the temperature of the sensor component is stabilized and correct. Once the first calibration measurement is completed, calibration reservoir 84b, including the second calibration solution, is ruptured and the solution directed into the delivery device. The temperature of the sensor component is again stabilized and corrected. The second calibration point is then established and the catheter is ready for use.

In each of the above-described embodiments, the sensor component may be brought to first calibration point conditions by utilizing a specifically equilibrated hydration solution. The hydration solution is equilibrated with a gaseous composition equivalent to that used to create the first calibration solution. When the first calibration point conditions are achieved in this manner, only one calibration solution, that corresponding to the second calibration point conditions, need be introduced to the sensor component during calibration. This reduces the steps required to prepare the catheter for use. Similarly, if the package is for a medical device that requires the setting of only a single calibration point, then a properly equilibrated hydration solution is the only solution necessary to prepare the device for use. In such an instance, the plumbing need not include a calibration section for delivering calibration solution to the sensor component. To utilize such a device, the instrumentation cables are removed from the packaging and connected to monitoring instrumentation. The sensor component is already immersed in the hydration solution that acts as the calibration solution. Calibration measurements are immediately taken and the device is then ready for use.

As an example of the relationships between the various solutions and the sensor component, if a blood gas catheter were to be used to measure pH, $PO_2$ and $PCO_2$, the buffer formulations for the calibration solutions would be selected to control the relationship between pH and $PCO_2$. Calibration solutions are characterized by their differing $PCO_2$ levels.

The following solution is a specific example of a solution that is suitable for use with the above-described catheter:

0.916 grams/liter potassium phosphate;
3.007 grams/liter sodium phosphate;
6.136 grams/liter sodium chloride; and
1.848 grams/liter sodium bicarbonate.

The solution is a bicarbonate-phosphate buffer which contains 105 mM sodium chloride which is the sodium chloride level that is substantially equivalent to that found in blood. The solution is adjusted with carbon dioxide gas and compressed air, or the equivalent oxygen/nitrogen mixture, to form the hydration and calibration solutions.

It has been found that the inclusion of sodium chloride in the preparation solutions is useful to reduce perturbations in the measuring process that are caused by the existence of predominate ions other than the targeted analyte(s) in the solution being monitored. In blood, sodium chloride is a predominate ionic compound that is not monitored by the blood gas catheter of the example. If the preparation solutions in which the sensor component is hydrated and calibrated do not contain the chloride component, an ionic gradient is created across the sensor component membrane when the sensor component is actually used in blood. This gradient effects the subsequent monitoring information received from the sensor component.

A suitable time and temperature for incubation of such a $PCO_2$, $PO_2$ and pH sensor has been found to be at least 7 days at a temperature of approximately 20° C. This incubation is adequate to bring the sensor component of the catheter to calibration conditions reflected in the amount and type of chemicals included in the gaseous mixture. Prior to use, it is preferable to again incubate the entire package for approximately 7 days at a temperature substantially equivalent to the temperature at the point of use. For an in situ blood gas catheter, the temperature range for the second incubation is 37° to 40° C. The second incubation has been found to improve the pH response time of the catheter. The catheter is then in a state for final calibration and use.

While preferred embodiments of the invention have been illustrated and described, it will be appreciated that various changes can be made herein without departing from the spirit and scope of the invention. Other methods and devices for holding and delivering the solutions in the manifold are available. For example, the solutions could be held directly in the envelopes and the plumbing means could include stopcocks for controlling the flow of the solutions from the envelopes into the plumbing means. Additionally, directional valves or other fittings are suitable for use in place of the stopcocks.

Many of the specific characteristics of the preferred embodiments depend upon material compatibility and the specific sensor component of the packaged device. For example, if a strong gas-impermeable clear material through which the stopcocks are adjustable is available and compatible with the procedures, this material is suitable for forming inner wrap 16. If this inner wrap is gas-impermeable, with the exception of filler 61, then the device is storable over an extended period of time without the outer wrap once the gas-permeable portions of the inner wrap are somehow sealed. This is also the case if the sensor component is held in a gas-impermeable plumbing section. The process of creating a constant gaseous environment about the plumbing for storage and incubation purposes is not necessary if the delivery device itself is gas-impermeable.

Other means for sealing off filter 61 during storage are available. The filter is covered with a seal patch, or the wrap portion including the filter is separated from the remainder of the wrap by a seal through the sides 60a and 60b of the inner wrap. In an alternative configuration, one or both sides 60a and 60b of inner wrap 16 are made of TYVEK membrane, or other suitable gas-permeable material, to increase the gas exchange rate through the inner wrap. In these embodiments, a gas-impermeable chamber is formed within which the gaseous environment about the plumbing is held during storage. The chamber may be formed by means of an outer wrap as described above.

Further, if a suitable ring and seal material are used, calibration tube 44 may be positioned outside of the package. In one embodiment, the calibration solution is then delivered through the calibration tube without breaching the wrap. Similarly, if the cables of the medical device are connectible to the monitoring instrumentation without breaching the wrap, the device is maintained in a sterile environment during the calibration procedure.

Finally, it is to be understood that the package and method of packaging of the present invention are not limited to blood gas catheters. The configuration of the sensor component of a specific device may dictate alternative configurations for the packaging.

The embodiments of the invention in which an exclusive property or privilege is claimed are defined as follows:

1. A package for a medical device, comprising:
a wrap enveloping a medical device, first and second reservoirs, and plumbing means, said wrap comprising a gas-permeable surface,
said medical device comprising a hydratable sensor component,
said first reservoir being substantially filled with a hydration solution suitable for hydrating said sensor component,
said second reservoir being substantially evacuated, and
said plumbing means being adapted to reversibly establish, without breaching said wrap, either gaseous communication between said gas-permeable surface and said sensor component or liquid communication between said first reservoir, said sensor component, and said second reservoir.

2. A package according to claim 1, further comprising means for defining a gas-impermeable chamber comprising the ambient environment of said plumbing means within said wrap.

3. A package according to claim 2, wherein said means for defining a gas-impermeable chamber comprises a bag enveloping said wrap.

4. A package according to claim 1, further comprising means for delivering said hydration solution from said first reservoir into said plumbing means.

5. A package according to claim 4, wherein said first reservoir is rupturable by said delivery means.

6. A package according to claim 1, wherein said sensor component comprises at least one optical fiber.

7. A package according to claim 1, wherein said plumbing means is adapted to reversibly establish fluid communication between the ambient environment of the package, said sensor component, and said second reservoir.

8. A package according to claim 7, wherein said plumbing means establishes fluid communication between the ambient environment of the package, the sensor component, and said second reservoir by breaching said wrap at a point remote from said sensor component, whereby said sensor component is maintained in a clean environment during the calibration procedure.

9. A package according to claim 1, further comprising a third reservoir substantially filled with a calibration solution suitable for calibrating said sensor component, wherein said plumbing means is adapted to reversibly establish, without breaching said wrap, liquid communication between said third reservoir, said sensor component, and said second reservoir.

* * * * *

UNITED STATES PATENT AND TRADEMARK OFFICE
CERTIFICATE OF CORRECTION

PATENT NO. : 4,863,016

DATED : September 5, 1989

INVENTOR(S) : Grabenkort et al.

It is certified that error appears in the above-identified patent and that said Letters Patent is hereby corrected as shown below:

On the title page

[75] Inventors, lines 1 & 2: Delete "Conrad T. O. Fong, Redmond, Wash."
[75] Inventors, line 4: Insert --Sheldon M. Wecker, Libertyville, Il.--
[57] Abstract, line 29: "enviroment" should be --environment--
Column 3, line 32: "Accordingly" should be --Additionally--
Column 7, line 31: "77" should be --70--
Column 7, line 37: "betwen" should be --between--
Column 11, line 21: "in situ" should be --in situ--

Item (19), "Fong, et al" should read -- Grabenkort, et al --.

Signed and Sealed this

Twentieth Day of November, 1990

Attest:

HARRY F. MANBECK, JR.

*Attesting Officer*      *Commissioner of Patents and Trademarks*